US006492328B2

(12) United States Patent
Lehrer et al.

(10) Patent No.: US 6,492,328 B2
(45) Date of Patent: Dec. 10, 2002

(54) NOVISPIRINS: ANTIMICROBIAL PEPTIDES

(75) Inventors: Robert I. Lehrer, Santa Monica; Alan J. Waring, Irvine, both of CA (US); Brian F. Tack, Iowa City, IA (US)

(73) Assignees: The University of Iowa Research Foundation, Iowa City, IA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 09/840,009

(22) Filed: Apr. 19, 2001

(65) Prior Publication Data

US 2002/0082195 A1 Jun. 27, 2002

Related U.S. Application Data

(63) Continuation-in-part of application No. 09/606,858, filed on Jun. 28, 2000, now abandoned.

(51) Int. Cl.[7] .................. A61K 38/00; A61K 38/04; C07K 7/00; C07K 16/00; C07K 17/00; C07K 5/00
(52) U.S. Cl. .................. 514/2; 530/300; 530/326
(58) Field of Search .................. 514/2; 530/300, 530/326

(56) References Cited

PUBLICATIONS

Mahoney, M. M. et al., "Molecular analysis of the sheep cathelin family reveals a novel antimicrobial peptide", FEBS Letters, vol. 377, pp. 519–522 (1995).*
SwissProt accession No. P49928, Cathelin–related peptide SC5 precursor 1, Oct. 1, 1996.*
SwissProt accession No. P49929, Cathelin–related SC5 precursor 2, Oct. 1, 1996.*
Brogden et al. (1998), "Detection of Small, Anionic Antimicrobial Peptides in Bronchoalveolar Lavage Fluid and Respiratory Epithelium of Patients with and without Cystic Fibrosis–1998 Cystic Fibrosis Conference." Pediatric Pulmonolgy, Supplement 17, Abstract No. 587.

Giacometti et al. (1999), "In–Vitro Activity of Cationic Peptides Alone and in Combination with Clinically Used Antimicrobial Agents Against Pseudomonas Aeruginosa." Journal of Antimicrobial Chemotherapy, vol. 44:641–645.
Gudmundsson et al. (1999), "Neutrophil Antibacterial Peptides, Multifunctional Effector Molecules in the Mammalian Immune System." Journal of Immunological Methods, vol. 232:45–54.
Hancock et al. (Feb. 1998), "Cationic Peptides: a New Source of Antibiotics." Tibtech, vol. 16:82–88.
Jia et al. (Sep. 1999), "Molecular Cloning and Characterization of Rat Genes Encoding Homologues of Human–Defensins." Infection and Immunity, vol. 67(9):4827–4833.
Lehrer et al. (1999), "Defensins and Other Antimicrobial Peptides" Mucosal Immunology, Chapter 6:89–99.
Takemura et al. (Oct. 1996), "Evaluation of Susceptibility of Gram–Positive and –Negative Bacteria to Human Defensins by Using Radial Diffusion Assay." Antimicrobial Agents and Chemotherapy, vol. 40(10):2280–2284.
Turner et al. (Sep. 1998), "Activities of LL–37, a Cathelin–Associated Antimicrobial Peptide of Human Neutrophils" Antimicrobial Agents and Chemotherapy, vol. 42(9):2206–2214.

* cited by examiner

Primary Examiner—Kenneth R. Horlick
Assistant Examiner—Teresa Strzelecka
(74) Attorney, Agent, or Firm—Pamela J. Sherwood; Bozicevic, Field & Francis LLP

(57) ABSTRACT

Novispirin peptides are antimicrobial agents with potent activity against Gram-negative bacteria. The peptides are nonhemolytic, exhibit reduced in vitro cytotoxicity relative to other antimicrobial peptides, and were well-tolerated in vivo after intravenous injection. Novispirins also bind lipopolysaccharide (LPS), a property that may mitigate symptoms associated with Gram-negative bacterial infection. A pharmaceutical composition comprising novispirin as an active agent is administered to a patient suffering from or predisposed to a microbial infection, particularly Gram-negative bacterial infections.

27 Claims, 7 Drawing Sheets

Bactericidal Kinetics. Activity against *P. aeruginosa* MR3007

Cytotoxicity of Novispirins against MRC-5 Lung Fibroblasts

NOVISPIRINS: ANTIMICROBIAL PEPTIDES

CROSS REFERENCE TO RELATED APPLICATIONS

This application is a continuation in part of U.S. patent application Ser. No. 09/1606,858, filed Jun. 28, 2000 now abandoned.

STATEMENT AS TO FEDERALLY SPONSORED RESEARCH

This invention was made with Government support under Grant no. A143934, awarded by the National Institutes of Health. The Government may have certain rights in this invention.

INTRODUCTION

Background

The development of effective antimicrobial agents was once seen as a definitive cure for bacterial diseases. But even before the development of the first antibiotics, bacteria had demonstrated an ability to adapt to stress in the environment, resulting in the development of resistance. In recent years, the variety of antimicrobial agents has increased substantially, along with a parallel increase in resistant pathogenic microorganisms. Resistance is now recognized against all clinically available antimicrobial agents. The response to antimicrobial resistance in the medical community has been to use new or alternative antibiotics not previously used against the resistant bacteria. This approach has required the continuous development of new antibiotics, either as modifications of currently existing compounds or as combinations of compounds that may inhibit or bypass the bacterial resistance mechanisms.

Natural polycationic antibiotic peptides have been found in many different species of animals and insects and shown to have broad antimicrobial activity. In mammals, these antimicrobial peptides are mainly represented by two families, the defensins and the cathelicidins. Nearly all of these peptides have membrane affinity, and can permeate and permeabilize bacterial membranes, resulting in injury, lysis, and/or death to the microbes. For example, the human peptides termed alpha-defensins are produced by neutrophils and intestinal Paneth cells. In three-dimensions, defensins manifest an amphiphilic, largely beta-sheet structure, with a polar face formed largely by its arginines and with N- and C-terminal residues playing an important role in defining antimicrobial potency and spectrum. (See Gudmundsson et al. (1999) *J Immunol Methods* 232(1–2): 45–54.) Antimicrobial peptides are reviewed by Hancock and Lehrer (1998) *Trends in Biotechnology* 16:82.

Cystic fibrosis (CF) is an inherited disorder that occurs in one of every 3,300 U.S. newborns. It affects some 30,000 Americans today. The median survival age of patients with CF is only 31.3 years, making CF the most common life-shortening inherited disease in the U.S. Most CF patients die from pulmonary failure that results from chronic, progressive infection by *Pseudomonas aeruginosa*—a Gram-negative bacterium that is widely distributed throughout the environment. *P. aeruginosa* has limited ability to infect normal individuals, but can be a devastating secondary invader in immunocompromised, severely burned, or antibiotic-treated persons. Because *Pseudomonas aeruginosa* strains frequently are or become resistant to conventional antibiotics, infections caused by them are often difficult to eradicate.

The in vitro activity of antimicrobial peptides, including cecropin P1, indolicidin, magainin II, nisin and ranalexin has been tested against clinical isolates of *P. aeruginosa*. The peptides were found to have a varied range of inhibitory values, and showed some synergy when combined with conventional antibiotics (Giacometti et al (1999) *J Antimicrob Chemother*. 44(5):641–5)

There is a clinical need for novel antibiotic agents that are active against drug resistant Gram-negative bacteria, and which have low toxicity against mammalian cells. The present invention addresses this need.

Relevant Literature

Saiman et al. (1999) Pediatr Pulmonol, Suppl. 17:320 report that drug resistant organisms from CF patients are inhibited by cathelicidin peptides; and Brogden et al. (1999) Pediatr Pulmonol, Suppl. 17:320 report on the efficacy of SMAP29 in an ovine model of pulmonary infection and its potential for treating *P. aeruginosa* infection in patients with cystic fibrosis (CF).

SUMMARY OF THE INVENTION

Methods and compositions are provided for the use of novispirin peptides. Novispirin peptides are small antimicrobial agents with potent activity against Gram-negative bacteria, including *Chlamydia trachomatis, Pseudomonas aeruginosa, Eschelichia coli* and *Stenotrophomonas maltophilia*. The peptides are nonhemolytic, exhibit reduced in vitro cytotoxicity relative to other antimicrobial peptides, and are well-tolerated in vivo after intravenous injection. Novispirins are equally effective against growing and stationary phase *P. aeruginosa*, and they retain activity in the presence of high concentrations of salt or human serum. Novispirins also bind lipopolysaccharide (LPS), a property that may mitigate symptoms associated with Gram-negative bacterial infection.

A pharmaceutical composition comprising novispirin as an active agent is administered to a patient suffering from a microbial infection, particularly bacterial infections. The protein is also effective at killing a variety of microbial organisms in vitro. Novispirin may be administered alone, or in combination with other bacteriocidal agents, e.g. antibiotics, as a cocktail of effective peptides, etc. Novispirin mediated killing of microbes is also useful for modeling and screening novel antibiotics.

DESCRIPTION OF THE SPECIFIC EMBODIMENTS

Figure 1B:
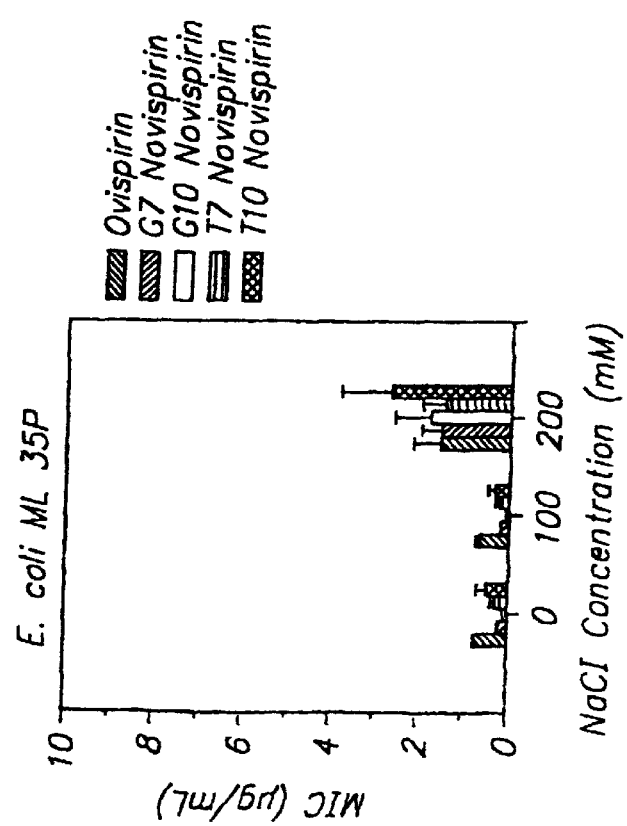
FIGS. 1A and 1B show the relative activity of ovispirin and representative novispirins against two Gram-negative bacteria.

Methods are provided for the use of novispirins as antimicrobial agents. The peptides are effective at killing a variety of microbial organisms in vitro and in vivo by direct microbicidal activity. Novispirin(s) are administered alone or in combination with other active agents to a patient suffering from or predisposed to an infection, in a dose and for a period of time sufficient to reduce the patient population of microbial pathogens.

There is a continuing need for new antimicrobial agents, particularly those that are effective in killing pathogens resistant to conventional antibiotics, e.g. *Pseudomonas aeruginosa*. Specific treatments of interest include, without limitation: aerosol administration to the lungs of patients with cystic fibrosis to treat infections caused, e.g. by *P. aeruginosa, S. maltophilia*, etc., and to forestall the emergence of resistance to other inhaled antibiotics; instillation into the urinary bladder of patients with indwelling catheters to prevent infection; application to the skin of patients with serious burns; opthalmic instillation, directly or in ophthalmic solutions, to treat or prevent infection; intravaginal application to treat bacterial vaginosis and/or prevent sexually transmitted disease, e.g. by preventing infection with *Chlamydia trachomatis*. The novispirins also find use in the treatment of plant-pathogenic pseudomonads, in agricultural applications designed to prevent disease in and spoilage of food crops.

The peptide form of novispirins provides a basis for further therapeutic development, by modification of the polypeptide structure to yield modified forms having altered biological and chemical properties. The native or modified forms are formulated in a physiologically acceptable carrier for therapeutic uses, or are otherwise used as an antimicrobial agent.

Novispirin Compositions

For use in the subject methods, any of the provided novispirins, modifications thereof, or a combination of one or more forms may be used. Novispirins include peptides of the formula as follows:

SEQ ID NO:1 KNLRRX$_1$X$_2$RKX$_3$X$_4$HIIKKYG wherein X$_1$, X$_2$, X$_3$ and X$_4$ are independently selected from the group consisting of the D or L forms of glycine, threonione, serine and isoleucine, preferably glycine, threonine, serine, glutamic acid, aspartic acid, isoleucine, D-alanine and D-isoleucine, with the proviso that not more than 3 of the X residues are isoleucine. Preferred amino acids for the non-isoleucine residues are glycine, serine and threonine. Preferred are peptides wherein only one of X$_1$ X$_2$, X$_3$ and X$_4$ is selected from glycine, serine and threonine.

Without being limited by the theory for making these substitutions, it is believed that the cytotoxicity of the antimicrobial peptide ovispirin (SEQ ID NO:2) is related to its high degree of rigidity and amphipathicity. The substitution of glycine, threonine, serine, glutamic acid, aspartic acid, isoleucine, D-alanine or D-isoleucine for one of the isoleucine resides at positions 6, 7, 10 or 11 in ovispirin adds flexibility (glycine), breaks the alpha-helix (D-alanine (DA) or D-isoleucine (DI)) or adds a polar residue to disrupt the overly hydrophobic region.

Table A shows the primary sequences of ovispirin and exemplary novispirin peptides. Bolded letters indicate the residues that distinguish these novispirins from ovispirin.

| | SEQ ID NO: | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| ovispirin | 2 | K | N | L | R | R | I | I | R | K | I | I | H | I | I | K | K | Y | G |
| G6-novispirin | 3 | K | N | L | R | R | G | I | R | K | I | I | H | I | I | K | K | Y | G |
| T6-novispirin | 4 | K | N | L | R | R | T | I | R | K | I | I | H | I | I | K | K | Y | G |
| S6-novispirin | 5 | K | N | L | R | R | S | I | R | K | I | I | H | I | I | K | K | Y | G |
| E6-novispirin | 6 | K | N | L | R | R | E | I | R | K | I | I | H | T | I | K | K | Y | G |
| D6-novispirin | 7 | K | N | L | R | R | D | I | R | K | I | I | H | I | I | K | K | Y | G |
| DA6-novispirin | 8 | K | N | L | R | R | dA | I | R | K | I | I | H | I | I | K | K | Y | G |
| D16-novispirin | 9 | K | N | L | R | R | dI | I | R | K | I | I | H | I | I | K | K | Y | G |
| G7-novispirin | 10 | K | N | L | R | R | I | G | R | K | I | I | H | I | I | K | K | Y | G |
| T7-novispirin | 11 | K | N | L | R | R | I | T | R | K | I | I | H | I | I | K | K | Y | G |
| S7-novispirin | 12 | K | N | L | R | R | I | S | R | K | I | I | H | I | I | K | K | Y | G |
| E7-novispirin | 13 | K | N | L | R | R | I | E | R | K | I | I | H | I | I | K | K | Y | G |
| D7-novispirin | 14 | K | N | L | R | R | I | D | R | K | I | I | H | I | I | K | K | Y | G |
| DA7-novispirin | 15 | K | N | L | R | R | I | dA | R | K | I | I | H | I | I | K | K | Y | G |
| D17-novispirin | 16 | K | N | L | R | R | I | dI | R | K | I | I | H | I | I | K | K | Y | G |
| G10-novispirin | 17 | K | N | L | R | R | I | I | R | K | G | I | H | I | I | K | K | Y | G |
| T10-novispirin | 18 | K | N | L | R | R | I | I | R | K | T | I | H | I | I | K | K | Y | G |
| S10-novispirin | 19 | K | N | L | R | R | I | I | R | K | S | I | H | I | I | K | K | Y | G |
| E10-novispirin | 20 | K | N | L | R | R | I | I | R | K | E | I | H | I | I | K | K | Y | G |
| D10-novispirin | 21 | K | N | L | R | R | I | I | R | K | D | I | H | I | I | K | K | Y | G |
| DA10-novispirin | 22 | K | N | L | R | R | I | I | R | K | dA | I | H | I | I | K | K | Y | G |
| DI10-novispirin | 23 | K | N | L | R | R | I | I | R | K | dI | I | H | I | I | K | K | Y | G |
| G11-novispirin | 24 | K | N | L | R | R | I | I | R | K | I | G | H | I | I | K | K | Y | G |
| T11-novispirin | 25 | K | N | L | R | R | I | I | R | K | I | T | H | I | I | K | K | Y | G |
| S11-novispirin | 26 | K | N | L | R | R | I | I | R | K | I | S | H | I | I | K | K | Y | G |
| E11-novispirin | 27 | K | N | L | R | R | I | I | R | K | I | E | H | I | I | K | K | Y | G |
| D11-novispirin | 28 | K | N | L | R | R | I | I | R | K | I | D | H | I | I | K | K | Y | G |
| DA11-novispirin | 29 | K | N | L | R | R | I | I | R | K | I | dA | H | I | I | K | K | Y | G |
| DI11-novispirin | 30 | K | N | L | R | R | I | I | R | K | I | dI | H | I | I | K | K | Y | G |
| G10-novispirin amide | 31 | K | N | L | R | R | I | I | R | K | G | I | H | I | I | K | K | Y | G-CONH$_2$ |
| G10, R12-novispirin | 32 | K | N | L | R | R | I | I | R | K | G | I | R | I | I | K | K | Y | G |
| G10, R12-novispirin | 33 | K | N | L | R | R | I | I | R | K | G | I | R | I | I | K | K | Y | G-CONH$_2$ |
| R2,G10-novispirin | 34 | K | R | L | R | R | I | I | R | K | G | I | H | I | I | K | K | Y | G |
| R2,G10-novispirin amide | 35 | K | R | L | R | R | I | I | R | K | G | I | H | I | I | K | K | Y | G-CONH$_2$ |

-continued

| | SEQ ID NO: | |
|---|---|---|
| R1,R2,G10-novispirin | 36 | R R L R R I I R K G I R I I K K Y G |
| R1,R2,G10-novispirin amide | 37 | R R L R R I I R K G I R I T K K Y G-CONH$_2$ |

The sequence of the novispirin polypeptides may also be altered in various ways known in the art to generate targeted changes in sequence. The polypeptide will usually be substantially similar to the sequences provided herein, i.e. will differ by one amino acid, and may differ by two amino acids. The sequence changes may be substitutions, insertions or deletions.

The protein may be joined to a wide variety of other oligopeptides or proteins for a variety of purposes. By providing for expression of the subject peptides, various post-translational modifications may be achieved. For example, by employing the appropriate coding sequences, one may provide farnesylation or prenylation. In this situation, the peptide will be bound to a lipid group at a terminus, so as to be able to be bound to a lipid membrane, such as a liposome. In another example, the carboxy terminus of the peptide is amidated, thereby increasing the positive charge of the peptide.

The novispirins for use in the subject methods may be produced from eukaryotic or prokaryotic cells by recombinant methods, or may be synthesized in vitro as known in the art.

In one embodiment of the invention, the antimicrobial peptide consists essentially of the polypeptide sequence set forth in any one of SEQ ID NO:1, or SEQ ID NO:3 to SEQ ID NO:30. By "consisting essentially of" in the context of a polypeptide described herein, it is meant that the polypeptide is composed of the sequence set forth in the seqlist, which sequence may be flanked by one or more amino acid or other residues that do not materially affect the basic characteristic(s) of the polypeptide.

Methods of Use

Formulations of novispirins are administered to a host suffering from or predisposed to a microbial infection. Administration may be topical, localized or systemic, depending on the specific microorganism, preferably it will be localized. Generally the dose of novispirin will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. Novispirins are particularly useful for killing gram negative bacteria, including *Pseudomonas aeruginosa*, and *Chlamydia trachomatis*.

Novispirins are also useful for in vitro formulations to kill microbes, particularly where one does not wish to introduce quantities of conventional antibiotics. For example, novispirins may be added to animal and/or human food preparations. Novispirins may be included as an additive for in vitro cultures of cells, to prevent the overgrowth of microbes in tissue culture.

The susceptibility of a particular microbe to killing with novispirins may be determined by in vitro testing, as detailed in the experimental section. Typically a culture of the microbe is combined with novispirins at varying concentrations for a period of time sufficient to allow the protein to act, usually between about one hour and one day. The viable microbes are then counted, and the level of killing determined.

Microbes of interest, include, but are not limited to Gram-negative bacteria, for example: Citrobacter sp.; Enterobacter sp.; Escherichia sp., e.g. *E. coli*; Klebsiella sp.; Morganella sp.; Proteus sp.; Providencia sp.; Salmonella sp., e.g. *S. typhi, S. typhimurium*; Serratia sp.; Shigella sp.; Pseudomonas sp., e.g. *P. aeruginosa*; Yersinia sp., e.g. *Y. pestis, Y. pseudotuberculosis, Y. enterocolitica*; Franciscella sp.; Pasturella sp.; Vibrio sp., e.g. *V. cholerae, V. parahemolyticus*; Campylobacter sp., e.g. *C. jejuni*; Haemophilus sp., e.g. *H. influenzae, H. ducreyi*; Bordetella sp., e.g. *B. pertussis, B. bronchiseptica, B. parapertussis*; Brucella sp., Neisseria sp., e.g. *N. gonorrhoeae, N. meningitidis*, etc. Other bacteria of interest include Legionella sp., e.g. *L. pneumophila*; Listeria sp., e.g. *L. monocytogenes*; Mycoplasma sp., e.g. *M. hominis, M. pneumoniae*; Mycobacterium sp., e.g. *M. tuberculosis, M. leprae*; Treponema sp., e.g. *T. pallidum*; Borrelia sp., e.g. *B. burgdorferi*; Leptospirae sp.; Rickettsia sp., e.g. *R. rickettsii, R. typhi*; Chlamydia sp., e.g. *C. trachomatis, C. pneumoniae, C. psittaci*; Helicobacter sp., e.g. *H. pylori*, etc.

Non bacterial pathogens of interest include fungal and protozoan pathogens, e.g. Plasmodia sp., e.g. *P. falciparum*, Trypanosoma sp., e.g. *T. brucei*; shistosomes; Entaemoeba sp., Cryptococcus sp., Candida sp, e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific novispirin to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The novispirins may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing novispirins is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 $\mu$g to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing peptides are combined in an appropriate aqueous medium, conveniently a saline medium where the total solids will be in the range of about 1–10 weight percent. After intense agitation for short periods of time, from about 5–60 sec., the tube is placed in a warm water bath, from about 25–400° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules.

Formulations with Other Active Agents

For use in the subject methods, novispirins may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a novispirins formulation, e.g. interferon γ, tumor necrosis factor α, interleukin 12, etc.

Synthesis of Novispirin

The subject peptides may be prepared by in vitro synthesis, using conventional methods as known in the art. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly D isomers, e.g. D-alanine and Disoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

EXPERIMENTAL

The following examples are put forth so as to provide those of ordinary skill in the art with a complete disclosure and description of how to make and use the subject invention, and are not intended to limit the scope of what is regarded as the invention. Efforts have been made to i ti ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

METHODS

Antimicrobial activity. Several different methods were used to examine the antimicrobial properties of novispirins, including: a) two-stage radial diffusion assays; b) colony counting assays; and c) standard microbroth dilution assays.

Antimicrobial activity was tested in media with low, normal or high salinity. In radial diffusion assays, this was accomplished by using a low salt "basic medium" containing 0.3 mg of trypticase soy broth powder/ml of 10 mM sodium phosphate buffer, pH 7.4. Media with "normal" or "high" salinity were prepared by supplementing the basic medium with 100 mM NaCl to obtain media with normal salinity, or with 175–200 mM NaCl to obtain high salt media. Retention of activity against *P. aeruginosa* in high salt media is important because airway fluids from cystic fibrosis patients are reported to show hypersalinity, and other sites—including skin surfaces surfaces and the urinary bladder—may have locally high salt concentrations.

Microorganisms used in this study included 13 different *Pseudomonas aeruginosa* strains. The AML-654 and LZ-1 strains are recent clinical isolates from the UCLA Clinical Microbiology laboratory. Nine strains (5 mucoid, 4 nonmucoid) were recent CF isolates provided by Dr. Lisa Saiman. All of the *P. aeruginosa* strains except PAO-1 strain were resistant to multiple conventional antibiotics, and all 9 CF isolates were resistant to 250 µg/ml of tobramycin. We have also tested 5 strains each of Stenotrophomonas maltophilia and Burkholderia cepacia from CF patients (also provided by Dr. Lisa Saiman), two strains of *Escherichia coli* (ML-35p and DH-5a), and single strains of *Staphylococcus aureus*[MRSA (methicillin-resistant *S. aureus*)] and *C. albicans*.

Cytotoxicity: A tetrazolium reduction assay (Boehringer-Mannheim, Indianapolis IN) was used to study cytotoxicity. ME-180 human cervical epithelial cells (ATCC HTB-33) and A549 human lung epithelial cells (ATCC CCL-185) were grown to confluency in RPMI Medium (ME-180) or Ham's F12K medium with 2 mM L-glutamine (A-549) containing 10% fetal bovine serum, 2 mM L-glutamine and 50 µg/mL gentamicin ("medium"). The cells were harvested with trypsin-XEDTA, washed with medium, and after their concentration and viability (trypan blue exclusion) was determined, they were diluted to $5 \times 10^4$ cells/mL. Aliquots (100 µl) were dispensed into 96 well tissue culture plates (Costar) and incubated for 5 hr. at 37° C. in room air with 5% $CO_2$. Then, serially diluted peptides were added and after 20 hr. of additional incubation, 10 μl of MTT solution was added. Four hours later, 100 μl of solubilization buffer was added and left overnight. The following day, MTT reduction was determined by optical density measurements at 600 and 650 nm, using a Spectramax 250 Spectrophotometer (Molecular Devices, Sunnyvale, Calif.).

Hemolytic Activity: This was tested by incubating various concentrations of peptide with a suspension (2.8% v/v) of washed human, murine, sheep or bovine red cells in PBS. After 30 min at 37C, the tubes were centrifuged and the percentage of total hemoglobin released to the supernatant was measured.

RESULTS

Antimicrobial Properties. Ovispirin and novispirins manifested potent antimicrobial activity against Gram-negative bacteria, including 13/13 strains of *Pseudomonas aeruginosa*. Eleven of these strains, including 9 (5 mucoid, 4 nonmucoid) from patients with cystic fibrosis, were recent clinical isolates. All of the CF strains were resistant to 250 μg/ml of tobramycin, and most were highly resistant to multiple additional antibiotics. Novispirins were also active against 5/5 strains of *Stenotrophomonas maltophilia*, an emerging pathogen in cystic fibrosis that is often resistant to conventional antibiotics. Like many other antibiotics and antimicrobial peptides, novispirins were inactive against *Burkholderia cepacia*.

Novispirin-mediated bactericidal activity occurred within 5–15 minutes, most likely from permeabilization of the inner and outer membranes of the bacteria. Antimicrobial activity was maintained under high salt (175–200 mM NaCl) conditions and was minimally impacted by the presence of 20% serum. Novispirins were equally effective against growing or quiescent *P. aeruginosa*.

Figure 1A:
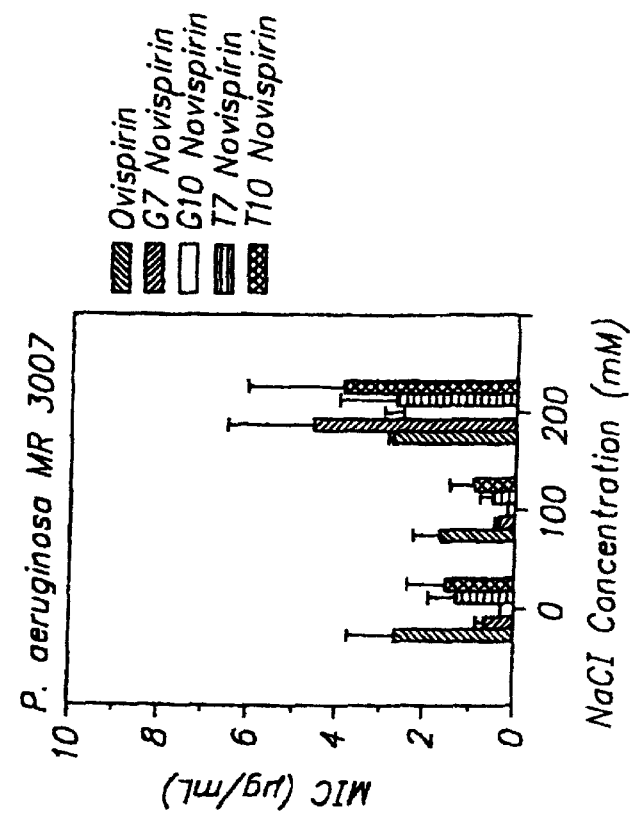

The relative activities of ovispirin and the novispirins against two organisms, *E. coli* and a multi-resistant strain of *P. aeruginosa*, are shown in FIG. 1. The MICs were obtained by radial diffusion assays performed under low, normal, and high salt conditions (which are denoted along the X-axis as 0, 100 and 200 mM NaCl, respectively). The bars show mean MIC values±SEM (n=3). It can be seen that novispirins were more active than ovispirin when tested under conditions of low and normal salinity, and about equally active under conditions of high salinity.

Table 1 compares the activity of novispirins against these Gram-negative bacteria with its activity against *Listeria monocytogenes, Staphylococcus aureus* and *C. albicans*. The tabulated data derive from radial diffusion assays and show (in μg/ml) the mean MIC±SEM, n=3. Note that novispirins show activity against these Gram-positive bacteria when tested in physiological (100 mM NaCl) salt concentrations, and also that Novispirin G10 is quite active against *C. albicans*. Although neither ovispirin nor novispirins retained activity against *C. albicans* or the Gram positives under very high salt conditions (200 mM NaCl), they remained active against the Gram-negatives under these conditions. Consequently, even if the airways' NaCl concentrations are exceptionally high in CF patients, this factor will not impair the ability of ovispirin or novispirins to kill *P. aeruginosa*.

TABLE 1

MIC (μg/mL) against 5 different organisms, [Mean ± SEM, n = 3]

| Peptide | E. coli ML 35P | P. aerugin. MR 3007 | L. mono. EGD | S. aureus 930918-3 | C. albicans 820 |
|---|---|---|---|---|---|
| Low Salt (+0 mM NaCl) | | | | | |
| Ovispirin | 0.7 ± 0.0 | 2.7 ± 1.1 | 2.0 ± 0.5 | 2.1 ± 0.3 | 2.2 ± 0.2 |
| $G_7$ Novispirin | 0.2 ± 0.0 | 0.6 ± 0.2 | 0.4 ± 0.1 | 0.6 ± 0.2 | 0.5 ± 0.1 |
| $G_{10}$ Novispirin | 0.1 ± 0.0 | 0.3 ± 0.0 | 0.2 ± 0.0 | 0.3 ± 0.0 | 0.2 ± 0.1 |
| $T_7$ Novispirin | 0.3 ± 0.1 | 1.3 ± 0.6 | 0.5 ± 0.2 | 0.7 ± 0.3 | 0.5 ± 0.2 |
| $T_{10}$ Novispirin | 0.5 ± 0.2 | 1.5 ± 0.9 | 0.6 ± 0.3 | 1.0 ± 0.6 | 0.8 ± 0.4 |
| Normal salinity (+100 mM NaCl) | | | | | |
| Ovispirin | 0.7 ± 0.1 | 1.7 ± 0.6 | 1.5 ± 0.3 | 1.0 ± 0.1 | 29.9 ± 15.4 |
| $G_7$ Novispirin | 0.2 ± 0.0 | 0.4 ± 0.1 | 2.3 ± 0.5 | 5.1 ± 1.1 | 9.3 ± 4.9 |
| $G_{10}$ Novispirin | 0.1 ± 0.0 | 0.2 ± 0.0 | 1.4 ± 0.4 | 4.6 ± 1.7 | 4.6 ± 1.9 |
| $T_7$ Novispirin | 0.2 ± 0.1 | 0.5 ± 0.3 | 2.4 ± 1.5 | 3.3 ± 1.5 | 18.6 ± 5.9 |
| $T_{10}$ Novispirin | 0.3 ± 0.2 | 0.9 ± 0.5 | 5.5 ± 4.0 | 9.7 ± 4.6 | 23.0 ± 3.9 |
| Very high salinity (+200 mM NaCl) | | | | | |
| Ovispirin | 1.5 ± 0.6 | 2.7 ± 0.1 | 3.3 ± 0.1 | 2.9 ± 0.7 | >250 |
| $G_7$ Novispirin | 1.5 ± 0.4 | 4.5 ± 1.9 | 28.2 ± 0.7 | 39.6 ± 9.2 | >250 |
| $G_{10}$ Novispirin | 1.8 ± 0.8 | 2.5 ± 0.5 | 9.3 ± 1.3 | 75.0 ± 51.5 | 205 ± 22.6 |
| $T_7$ Novispirin | 1.4 ± 0.5 | 2.7 ± 1.3 | 21.5 ± 2.0 | 14.9 ± 2.9 | >250 |
| $T_{10}$ Novispirin | 2.7 ± 1.1 | 3.9 ± 2.1 | 26.8 ± 1.6 | 75.3 ± 56.2 | >250 |

TABLE 2

Microbroth dilution assay *P. aeruginosa* PAO1 (μg/ml, mean values, n = 3)

| | MIC | | | MBC | | |
|---|---|---|---|---|---|---|
| | mM NaCl | | | | | |
| Peptide | 0 | 100 | 175 | 0 | 100 | 175 |
| Ovispirin | 3.1 | 3.1 | 4.7 | 4.7 | 7.1 | 9.4 |
| $G_7$ Novispirin | 1.6 | 6.8 | 4.4 | 2.6 | 14.1 | 8.3 |
| $G_{10}$ Novispirin | 2.6 | 16.1 | 11.3 | 6.8 | 16.7 | 29.2 |
| $T_7$ Novispirin | 2.1 | 3.9 | 5.7 | 7.3 | 6.3 | 12.5 |
| $T_{10}$ Novispirin | 2.8 | 5.7 | 2.8 | 6.8 | 9.4 | 9.4 |
| Protegrin PG1 | 2.1 | 2.6 | 2.6 | 3.2 | 2.7 | 3.5 |

*P. aeruginosa* within the airways of patients with cystic fibrosis can differ in many ways from free-living planktonic members of the species. Among these differences are: their entrapment in an alginate-rich biofilm, selection for auxotrophy and antibiotic resistance, various modifications to their lipid and LPS structures, and metabolism characteristic of high density, nutrient-limited cultures. Many conventional antibiotics (e.g., inhibitors of cell wall or protein synthesis) and many antimicrobial peptides act preferentially against rapidly growing organisms and might therefor be relatively inactive against high mass/low turnover populations of bacteria. We therefor tested the activity of ovispirin and novispirins against 3 strains of *P. aeruginosa*, PAO-1, Liz-1 and AML654 to see if the peptides could kill stationary phase or nutritionally-starved organisms as well as rapidly growing ones. All three strains gave equivalent results. Table 3 shows data for PAO-1 and Liz-1 strains. Note that neither the growth phase nor the presence or absence of nutrients affected the susceptibility of *P. aeruginosa* to novispirins.

TABLE 3

Activity of peptides against growing and stationary phase *P. aeruginosa* (2 strains), tested with and without the presence of nutrients (TSB) in the underlay gel

| Peptide | MIC ($\mu$g/mL) *P. aeruginosa* PAO1/*P. aeruginosa* Liz-1 | | | |
|---|---|---|---|---|
| | Mid-log 1% TSB | Mid-log No TSB | Stationary 1% TSB | Stationary no TSB |
| Low Salt | | | | |
| Ovispirin | 0.6/1.8 | 1.3/1.1 | 1.8/1.9 | 0.9/2.0 |
| G7 novispirin | 0.4/0.4 | 0.3/0.6 | 0.4/0.3 | 0.3/0.6 |
| G10 novispirin | 0.3/0.3 | 0.1/0.4 | 0.3/0.1 | 0.2/0.4 |
| T7 novispirin | 0.4/0.6 | 0.5/0.6 | 0.6/0.4 | 0.5/0.7 |
| T10 novispirin | 0.6/0.7 | 0.6/1.0 | 0.9/0.9 | 0.6/0.9 |
| 100 mM NaCl | | | | |
| Ovispirin | 0.9/1.6 | 0.9/1.4 | 1.5/1.5 | 0.9/2.1 |
| G7 novispirin | 0.2/0.2 | 0.5/0.6 | 0.1/0.2 | 0.5/1.2 |
| G10 novispirin | 0.1/0.2 | 0.8/1.3 | 0.1/0.1 | 0.5/2.0 |
| T7 novispirin | 0.3/0.3 | 0.6/0.4 | 0.4/0.4 | 0.5/0.7 |
| T10 novispirin | 0.3/0.5 | 0.9/0.6 | 0.5/0.5 | 0.8/1.4 |
| 175 mM NaCl | | | | |
| Ovispirin | 1.2/0.9 | 0.9/0.7 | 1.1/1.2 | 0.8/0.8 |
| G7 novispirin | 1.2/2.1 | 0.2/0.1 | 1.0/2.9 | 0.1/0.1 |
| G10 novispirin | 3.6/5.9 | 0.1/0.1 | 4.7/5.9 | 0.1/2.3 |
| T7 novispirin | 0.8/2.0 | 0.3/0.1 | 0.8/2.0 | 0.2/0.6 |
| T10 novispirin | 2.3/3.4 | 0.3/0.2 | 1.9/3.0 | 0.4/0.8 |

Effect of serum. Human defensins and LL-37 (an α-helical human cathelicidin peptide) bind extensively to serum molecules. Consequently, their antimicrobial activity is greatly reduced if serum is present. Because serum can be present in an inflammatory focus or exudate, the ability to function in the presence of serum would be a desirable property. We recently found that SMAP-29, an α-helical cathelicidin found in sheep, retains its antimicrobial activity in the presence of serum, proving that serum inhibition is not an inevitability but a question of design. Table 4 shows the effect of serum on the activity (MIC) of novispirins, LL-37, SMAP-29 and other peptides against *P. aeruginosa* MR3007 (a serum-resistant strain) and *E. coli* ML-35P (sensitive to >5% serum). Ovispirin and novispirins lost some activity against *P. aeruginosa* in the presence of serum, but were affected much less than LL-37.

TABLE 4

Effect of normal human serum on antimicrobial activity

| | MIC ($\mu$g/mL) | | | | |
|---|---|---|---|---|---|
| | *E. coli* ML 35P | | *P. aeruginosa* MR 3007 | | |
| Peptide | 0% NHS | 2.5% NHS | 0% NHS | 2.5% NHS | 20% NHS |
| Ovispirin | 1.7 | 1.7 | 5.6 | 20.1 | 17.6 |
| G7 Novispirin | 0.5 | 0.4 | 7.5 | 21.5 | 17.7 |
| G10 Novispirin | 0.9 | 0.7 | 7.6 | 22.1 | 21.7 |
| T7 Novispirin | 1.0 | 0.7 | 7.5 | 25.2 | 22.0 |
| T10 Novispirin | 1.0 | 0.7 | 8.6 | 28.6 | 17.6 |
| PG-1 (protegrin) | 0.5 | 0.3 | 1.6 | 0.91 | 1.6 |
| PGG | 1.8 | 0.9 | 5.8 | 7.41 | 8.6 |
| SMAP-29 | 0.6 | 0.3 | 1.4 | 1.5 | 1.2 |
| LL-37 | 5.8 | 21.0 | 12.7 | 23.7 | 141 |

Figure 2:
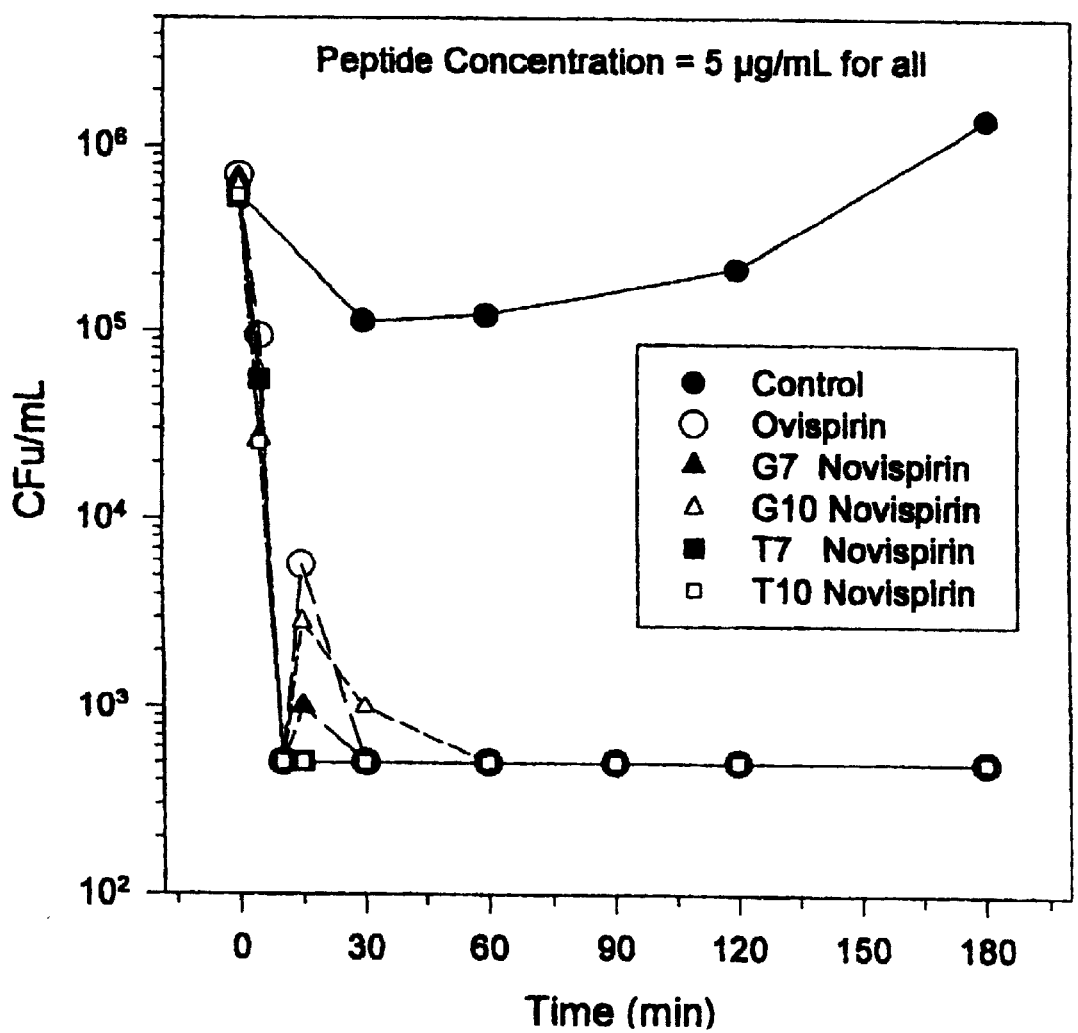
FIG. 2 shows the kinetics of antimicrobial peptides against *P. aeruginosa*.

In these experiments, the underlay gel contained 60% RPMI-1640, ±2.5 or 20% normal human serum (NHS). The remainder of the solution was phosphate-buffered saline Kinetics of Microbicidal activity. We measured the survival of *P. aeruginosa* MR3007 at intervals after it was exposed to 5 $\mu$g/ml of ovispirin or novispirins in a PBS medium that contained 1 % v/v trypticase soy broth. FIG. 2 shows a rapid 2–3 $\log_{10}$ fall and that no surviving bacteria were recovered by 30 minutes or thereafter.

Figure 3:
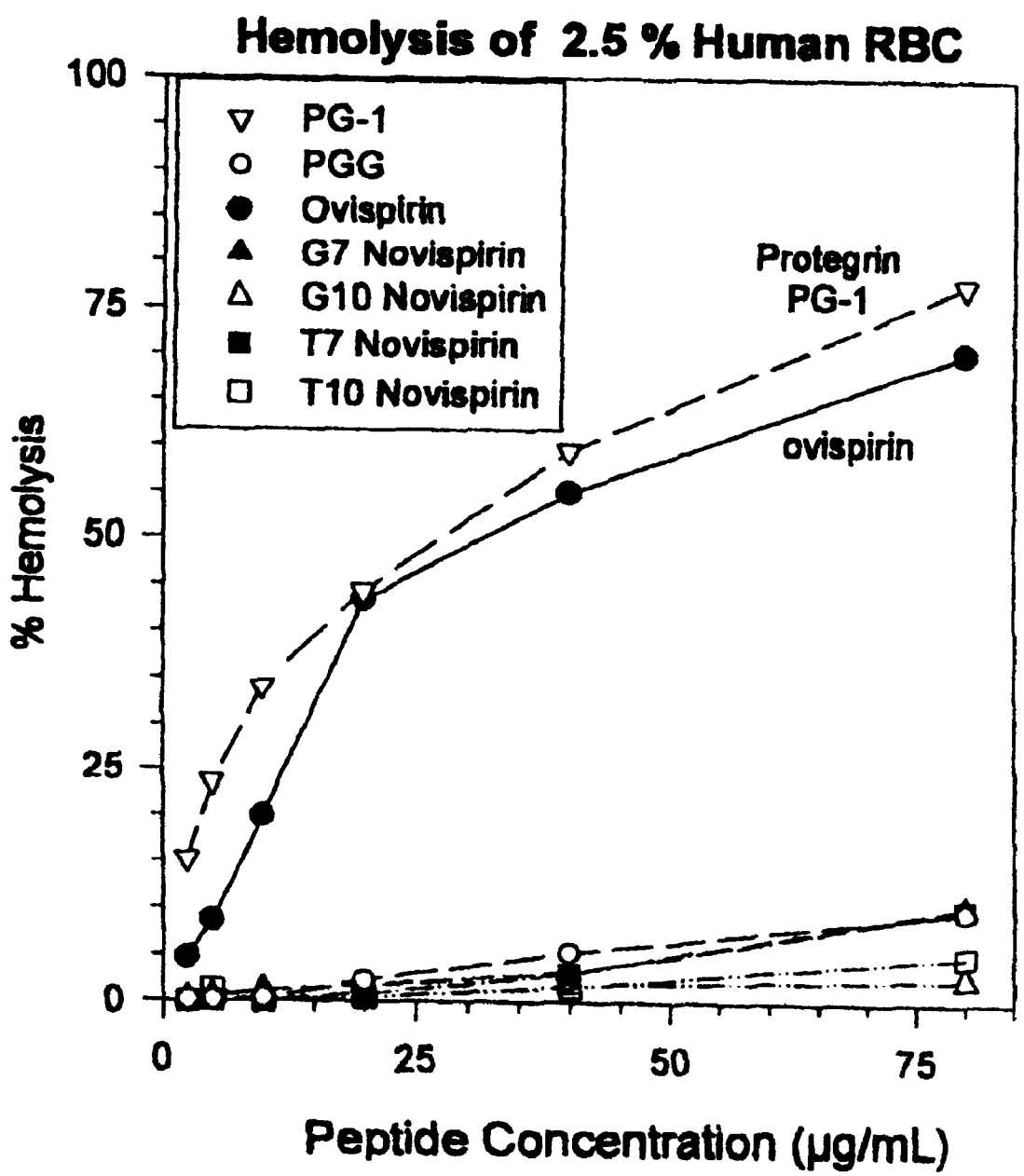
FIG. 3 shows the hemolytic activity of antimicrobial peptides against human red blood cells.

FIG. 3 shows the effect of ovispirin or novispirins in lysing red blood cells. Although ovispirin was about as hemolytic for human red blood cells as protegrin PG-1, the novispirins were non hemolytic. Similar results were obtained with murine red blood cells. In contrast, none of these peptides were appreciably hemolytic towards sheep or bovine red blood cells.

Figure 4B:
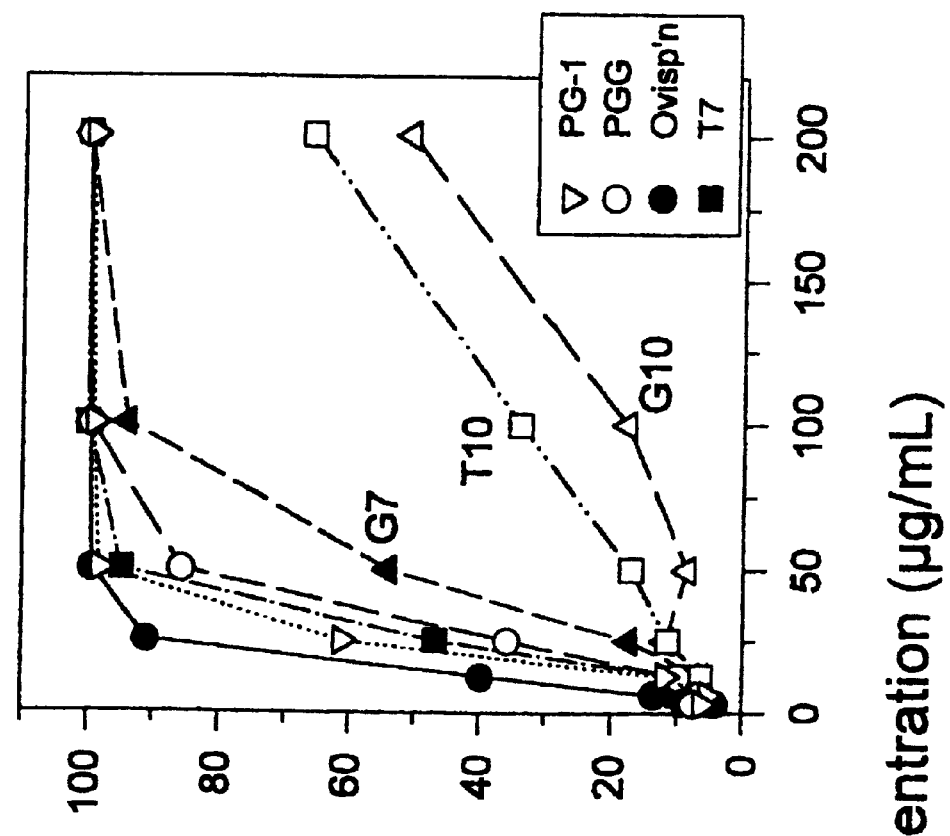
FIGS. 4A, 4B and 4C show the relative cytotoxicity of antimicrobial peptides against human cells.
Figure 4A:
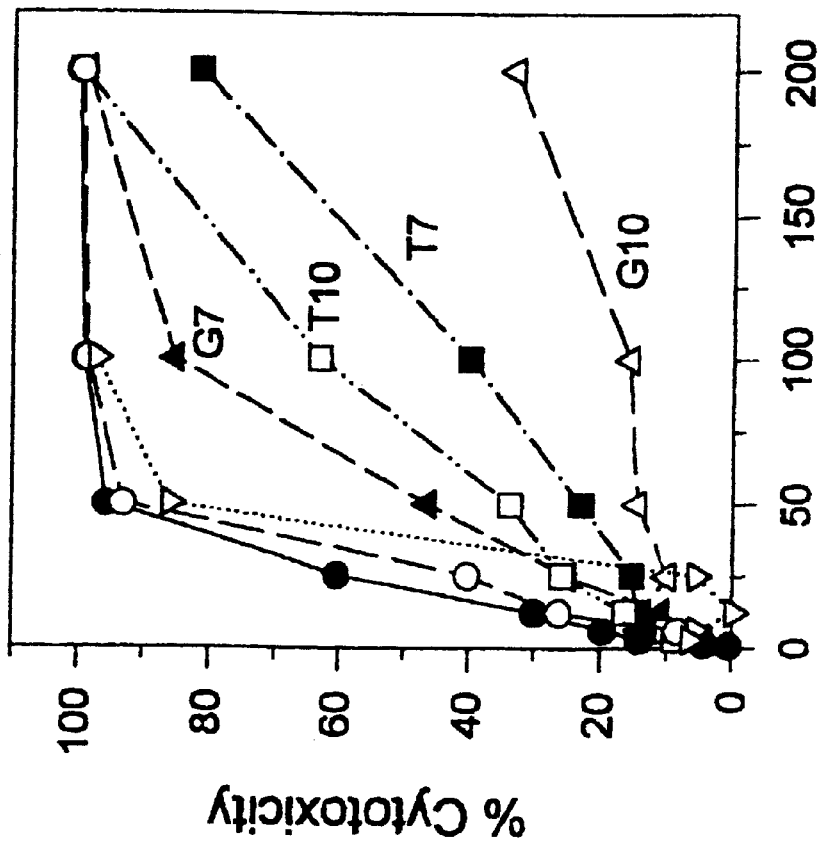
Figure 4C:
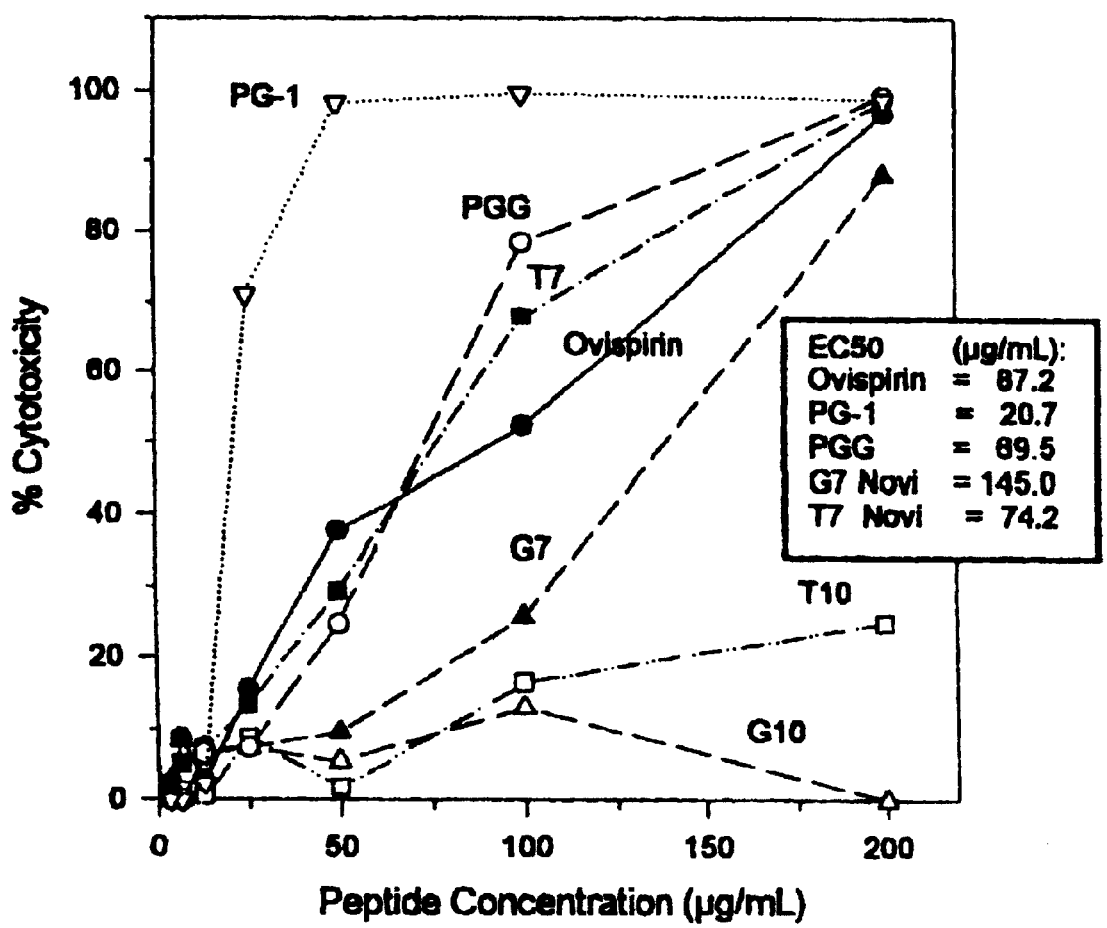

Cytotoxic properties. Novispirins, especially novispirin GI 0, were markedly less toxic towards human epithelial cells or fibroblasts than ovispirin or other antimicrobial peptides previously studied, e.g. protegrin PG-1, magainin MSI-78, or PGG. Representative assays for cytotoxicity against ME-180 human cervical epithelial cells and A-549 pulmonary epithelial cells are shown in FIG. 4.

Figure 5:
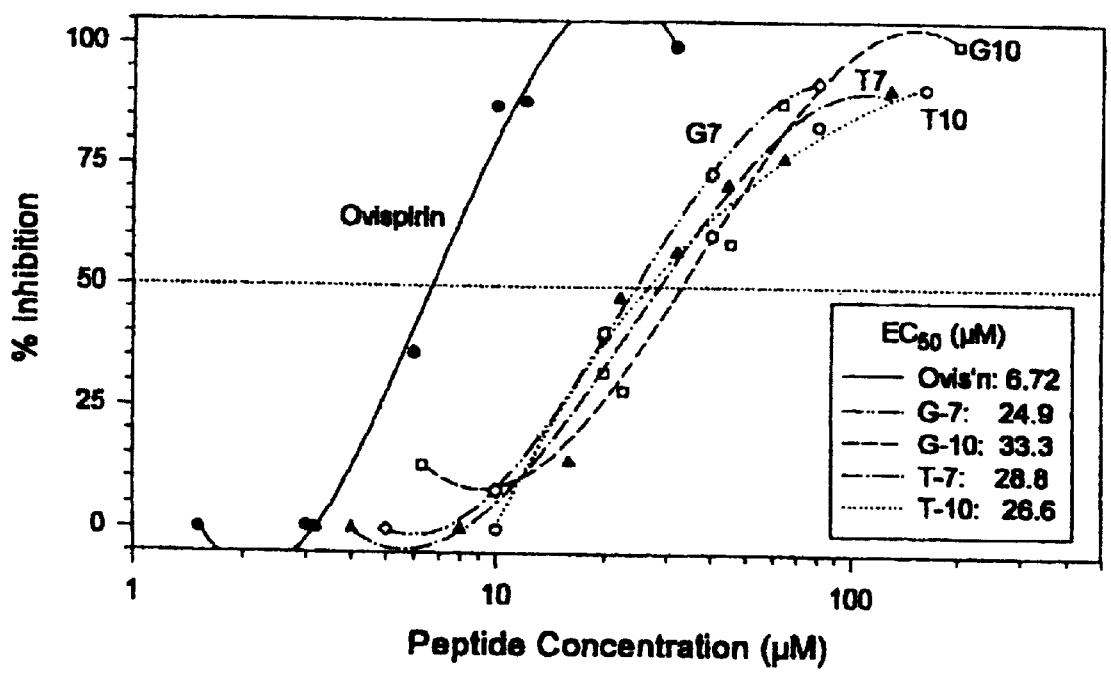
FIG. 5 shows the binding of LPS by novispirins.
Figure 6B:
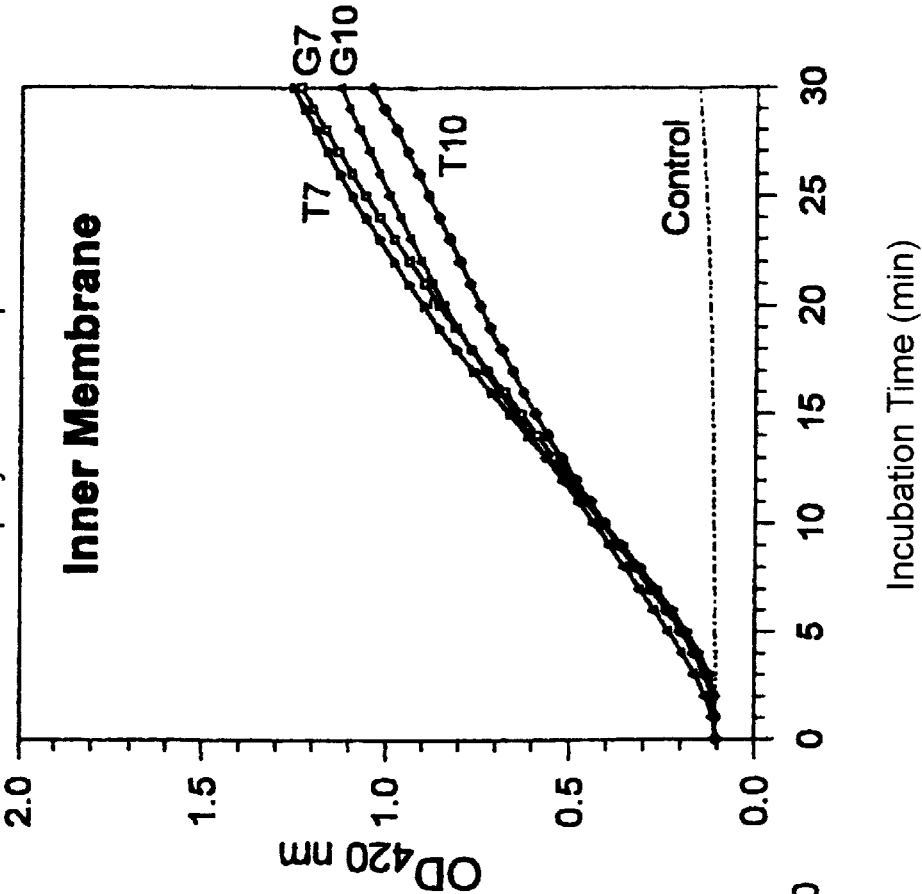
FIGS. 6A and 6B shows the permeabilization of bacterial membranes by novispirins.
Figure 6A:
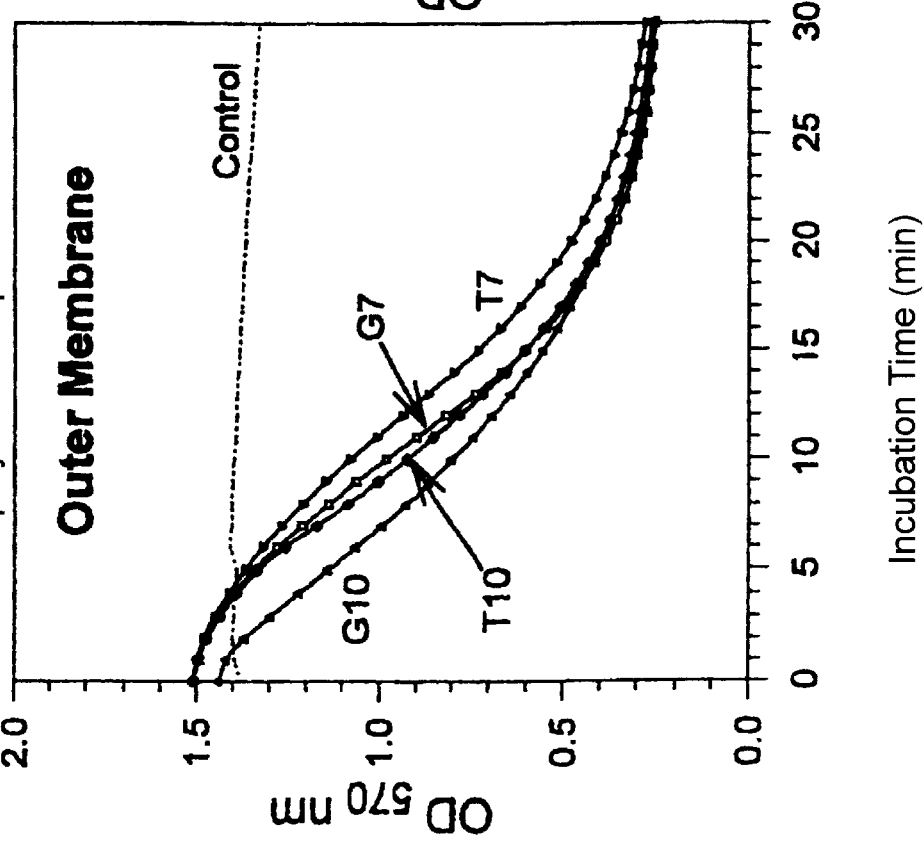

FIG. 5 compares the cytotoxicity of these peptides for MRC-5 human lung fibroblasts. The G10 and T10 novispirins were virtually devoid of cytotoxicity, demonstrating that they would be unlikely to retard tissue repair or wound healing.

In vivo toxicity. Acute toxicity studies were performed in mice. 3/3 mice survived an intravenous dose of 10 mg novispirin G10/kg body weight, and 1/3 survived a dose of 20 mg/kg. If the blood volume of a mouse constitutes 5% of its mass, then the 10 mg/kg dose would yield a peak level of approximately 200 micrograms/ml—some 20 to 50 fold higher than its MIC concentrations.

LPS Binding. We measured the ability of ovispirin and novispirins to bind LPS in two assays. One assay is spectrophotomentric, and uses a quantitative Limulus chromogenic assay. The other assay is physical, and measures surface plasmon resonance changes.

The apparent binding constant of ovispirin for LPS was approximately $6.7 \times 10^{-4}$M. When the binding assays were done under low salt conditions (0 mM NaCl), the affinity of novispirins was lower by a factor of 4–5, i.e., between 2.5 and $3.3 \times 10^{-5}$M. When we tested binding in physiological NaCl, the affinity of novispirins for LPS increased.

Effects of novispirins on bacterial membranes. All of the novispirins, when tested at 5 $\mu$g/ml, rapidly permeabilized the outer and inner membranes of *E. coli* M-35p. The onset of membrane permeabilization is rapid, beginning within 2 minutes and reaching maximal extent within 5 minutes. This experiment was performed with stationary phase *E. coli*, suspended in PBS (100 mM NaCl). Outer membrane permeabilization was measured by monitoring the hydrolysis of PADAC, a cephalosporin, and inner membrane permeabilization was measured by monitoring hydrolysis of ONPG (this *E. coli* strain has no lac permease.

Table 5 shows the activity of novispirins against *S. maltophila*.

TABLE 5

Novispirins vs *S. maltophilia*

| | 51Cl | 47CG | 18CP | 42CK | 36CN |
|---|---|---|---|---|---|
| LOW SALT CONDITIONS | | | | | |
| Protegrin PG-1 | 0.42 | 0.09 | 0.52 | 0.32 | 0.27 |
| PGG | 1.31 | 0.73 | 0.86 | 1.51 | 1.10 |
| Polymyxin B | 0.02 | 0.16 | 0.04 | 0.05 | 0.06 |
| Ovispirin | 1.60 | 0.07 | 1.46 | 1.73 | 1.01 |
| G7 novispirin | 0.54 | 0.25 | 0.61 | 0.42 | 0.17 |
| G10 novispirin | 0.45 | 0.08 | 0.40 | 0.43 | 0.15 |
| T7 novispirin | 0.88 | 0.18 | 0.74 | 0.56 | 0.21 |
| T10 novispirin | 0.97 | 0.21 | 0.88 | 0.77 | 0.32 |
| +100 mM NaCl | | | | | |
| Protegrin PG-1 | 0.92 | 0.53 | 0.58 | 0.50 | 0.46 |
| PGG | 2.20 | 1.08 | 1.63 | 2.67 | 1.05 |
| Polymxin B | 0.04 | 0.08 | 0.04 | 0.02 | 0.02 |
| Ovispirin | 2.20 | 0.54 | 0.88 | 1.24 | 0.93 |
| G7 nov. | 0.89 | 0.39 | 0.38 | 0.92 | 0.31 |
| G10 nov. | 3.57 | 0.68 | 0.70 | 0.67 | 0.29 |
| T7 nov. | 1.75 | 0.47 | 0.58 | 0.73 | 0.32 |
| T10 nov. | 5.02 | 0.75 | 0.88 | 1.27 | 0.48 |
| +175 mM NaCl | | | | | |
| Protegrin PG-1 | 1.08 | 0.74 | 0.70 | 0.79 | 0.57 |
| PGG | 2.85 | 1.64 | 2.34 | 7.10 | 1.11 |
| Polymyxin B | 0.05 | 0.05 | 0.002 | 0.01 | 0.02 |
| Ovispirin | 1.67 | 0.77 | 0.91 | 2.03 | 0.91 |
| G7 nov. | 1.94 | 0.29 | 0.70 | 2.85 | 0.29 |
| G10 nov. | 8.18 | 0.63 | 1.30 | 10.0 | 0.36 |
| T7 nov. | 2.74 | 0.48 | 0.62 | 1.92 | 0.52 |
| T10 nov. | 15.5 | 0.70 | 2.08 | 1.25 | 0.53 |

Protegrin PG-1, polymyxin B and PGG were used as controls.
PGG is an α-helical peptide, whose sequence is: GLLRRLRKKIGE-IFKKYG.
It was designed and reported by Tossi, A., Tarantino, C. and Romeo, D. 1997. Design of synthetic antimicrobial peptides based on sequence analogy and amphipathicity. Eur. J. Biochem. 250: 549–58.

EXAMPLE 2

Susceptibility of *Chlamydia Trachomatis* Serovars L2, D and E to G-10 Novispirin The susceptibility of three *Chlamydia Trachomatis* serovars (L2, D and E) to novispirin (G-10), a novel 18-residue a-helical peptide was assayed in this study. G-10 is non-hemolytic and has minimal cytotoxicity when tested against epithelial cells in vitro. It is relatively selective for Gram-negative organisms.

*C. trachomatis* serovar L2 causes invasive LGV, whereas serovars D and E represent typical genital strains. The effect of G-10 on *Chlamydia trachomatis* serovars (L2, D and E) was determined using standard and modified McCoy cell shell vial assays and varying concentrations of peptide. In the standard assay, the Chlamydia/peptide mixture was pre-incubated for 2 hr., then removed from the host cell monolayer before the 48-hr. incubation. In the modified assay, the pre-incubation mixture was left on the monolayer for the 48 hr. incubation. In a third assay, G-10 and Chlamydia were mixed and infected to cell monolayers without pre-incubation, and examined after 48 hr. Inclusion-forming units (IFUs) were scored to measure the peptide's inhibitory effect.

G-10 completely inhibited *C. trachomatis* serovar E at 100 μg/ml in the pre-incubation assays. At 100 mg/ml, serovar L2 IFUs were reduced by 92.7–99.1% and serovar D IFUs were reduced 99.4–100%. In general, omission of the pre-incubation step reduced susceptibility of Chlamydia to novispirin. Lack of removal of Chlamydia/peptide mixes did not increase or decrease susceptibility to G-10 significantly. G-10 is even more effective than protegrins, antimicrobial peptides found in porcine leukocytes that have excellent activity against *Chlamydia trachomatis*. In addition, all 3 serovars tested were susceptible to G-10. Novispirin is therefore shown to have utility as a chemoprophylactic agent to prevent chlamydial infections.

EXAMPLE 3

Effect of Divalent Cations on Novispirin Activity

The activity of G10 novispirin against certain bacteria is inhibited by approximately 1 mM concentrations of calcium and magnesium. This inhibition can be relieved by adding a citrate-containing buffer. Based on this finding, formulations of novispirins intended for topical use should contain citrate or another divalent cation binder, such as EDTA (ethylenediamine tetraacetic acid). The beneficial effect of a citrate-containing formulation on the activity of G10 Novispirin are shown below in Table 6.

Experiments which led to this finding involved the use of radial diffusion assays. All underlay gels contained 100 mM NaCl and 5 mM HEPES buffer (pH 7.4). In addition, some underlay gels were supplemented with 5 mM sodium citrate buffer, pH 7.4, while others contained 1 mM $CaCl_2$ or 1 mM $MgCl_2$. The numbers represent MIC values in μg/ml. Note that the enhancing effect of citrate was more prominent with Gram negative organisms than with S. aureus. EDTA, which is an even more effective chelator of calcium and magnesium, is expected to have the same effect as citrate.

TABLE 6

| Organism | Citrate | No Ca/Mg | +1 mM Ca | +1 mM Mg |
|---|---|---|---|---|
| K. pneumoniae | None | 0.12 | 116.0 | 8.37 |
| K. pneumoniae | 5 mM | 0.23 | 3.1 | 0.56 |
| P. aeruginosa | None | 0.18 | 22.7 | 1.35 |
| P. aeruginosa | 5 mM | 0.13 | 0.14 | 0.14 |
| E. coli | None | 0.16 | 9.3 | 2.56 |
| E. coli | 5 mM | 0.11 | 0.12 | 0.14 |
| S. aureus | none | 0.46 | 250.0 | 7.7 |
| S. aureus | 5 mM | 8.04 | 27.0 | 21.4 |

EXAMPLE 4

Three new variants of novispirin G10 were prepared and tested to determine if increasing the net positive charge of the peptide renders it more effective in the presence of divalent cations. Amidation (—NH2) of the carboxy terminus in some of the novispirin G10 variants was designed to increase overall positive charge. The sequences of these peptides and their net charge is shown below in Table 7. The fractional (and pH dependent) charge on $histidine_{12}$ was ignored in this calculation.

TABLE 7

| Peptide | Net charge | SEQ ID NO | Sequence |
|---|---|---|---|
| $G_{10}$ Novispirin | +7 | 17 | KNLRRIIRKG IHIIKKYG-COOH |
| $G_{10}$ Novispirin amide | +8 | 31 | K N L R R I I R K G I H I I K K Y G-CONH$_2$ |
| $G_{10}$, $R_{12}$ Novispirin | +8 | 32 | K N L R R I I R K G I R I I K K Y G-COOH |
| $G_{10}R_{12}$ Novi'n amide | +9 | 33 | K N L R R I I R K G I R I I K KY G-CONH$_2$ |

Results: MIC, mean ± SEM, n = 3. Shaded box indicates p < 0.01, compared to G10, by t-test.

TABLE 8

| Organism | Peptide | No Ca/Mg | +1 mM Ca | +1 mM Mg |
|---|---|---|---|---|
| S. aureus | Ovispirin | 0.49 ± 0.05 | 6.15 ± 0.12 | 5.93 ± 0.19 |
| | Novispirin G10 | 22.7 ± 2.1 | 99.0 ± 5.7 | >79 |
| | Novispirin G10 amide | ▓▓ | >79 | ▓▓ |
| | Novispirin G10, R12 | 23.0 ± 0.13 | >79 | 87.0 ± 5.7 |
| | Novispirin G10, R12 amide | ▓▓ | ▓▓ | ▓▓ |
| P. aeruginosa | Ovispirin | 2.31 ± 0.21 | 22.1 ± 1.78 | 7.18 ± 0.51 |
| | Novispirin G10 | 0.17 ± 0.04 | >250 | >250 |
| | Novispirin G10 amide | 0.12 ± 0.01 | 83.5 ± 6.4 | >250 |
| | Novispirin G10, R12 | 0.10 ± 0.01 | ▓▓ | ▓▓ |
| | Novispirin G10, R12 amide | 0.15 ± 0.04 | ▓▓ | ▓▓ |
| E. coli | Ovispirin | 0.8 ± 0.14 | 6.97 ± 0.42 | 6.99 ± 0.11 |
| | Novispirin G10 | 0.09 ± 0.02 | 21.2 ± 0.36 | 20.3 ± 0.1 |
| | Novispirin G10 amide | 0.06 ± 0.00 | 7.26 ± 0.02 | 17.2 ± 3.9 |
| | Novispirin G10, R12 | 0.05 ± 0.0 | ▓▓ | ▓▓ |
| | Novispirin G10, R12 amide | 0.06 ± 0.01 | ▓▓ | ▓▓ |
| K. pneumoniae | Ovispirin | 2.31 ± 0.02 | 22.1 ± 1.8 | 7.18 ± 0.5 |
| | Novispirin G10 | 0.17 ± 0.03 | >250 | >250 |
| | Novispirin G10 amide | 0.12 ± 0.01 | 83.5 ± 6.4 | >250 |
| | Novispirin G10, R12 | 0.10 ± 0.1 | ▓▓ | ▓▓ |
| | Novispirin G10, R12 amide | 0.15 ± 0.04 | ▓▓ | ▓▓ |

In Table 8, MIC signifies minimal inhibitory concentration, as determined by two stage radial diffusion assays. These were done under standard conditions, except that 10 mM HEPES buffer was used in place of 10 mM phosphate to avoid solubility problems when working with calcium. Shaded boxes show results that represent a significant improvement of activity (p<0.01 by t-test), relative to novispirin G10. Note that G10, R10 novispirin amide showed improved activity against all four test organisms in the presence of calcium and magnesium and that G10, R10 novispirin was more active against the three Gram negative organisms (*P. aeruginosa, E. coli* and *K. pneumoniae*) but was not more effective against *S. aureus*. None of the above G10 novispirin derivatives caused any hemolysis of human red blood cells, even when tested at 80 µg/ml. It is likely that other cationic amino acids (e.g., lysine, ornithine, etc) could also be used in position 12 to achieve better activity in the presence of calcium and magnesium ions.

EXAMPLE 5

Four variants of G10 novispirin were synthesized, to see if increasing the positive charge of the N-terminus can also increase resistance to calcium and magnesium. Amino acid sequence of these G10 variants are shown below in Table 9 with their respective net charge.

| Peptide | Net charge | SEQ ID NO: | Sequence |
|---|---|---|---|
| R2, $G_{10}$ Novispirin | +8 | 34 | K R L R R I I R K G I H I I K K Y G-COOH |
| R2, $G_{10}$ Novispirin amide | +9 | 35 | K R L R R I I R K G I H I I K K Y G-CONH$_2$ |
| R1, R2,G10 Novispirin | +8 | 36 | R R L R R I I R K G I R I I K K Y G-COOH |
| R1, R2,G10 Novisp'n amide | +8 | 37 | R R L R R I I R K G I R I I K K Y G-CONH$_2$ |

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antimicrobial polypeptide comprising the sequence, as set forth in SEQ ID NO:1, KNLRRX$_1$X$_2$RKX$_3$X$_4$HIIKKYG;
   wherein X$_1$, X$_2$, X$_3$ and X$_4$ are independently selected from the group consisting of the D or L forms of glycine, threonione, serine and isoleucine, with the proviso that not more than 3 of the X residues are isoleucine.

2. The antimicrobial peptide of claim 1, wherein X$_1$, X$_2$, X$_3$ and X$_4$ are independently selected from the group consisting of glycine, threonine, serine and, isoleucine, with the proviso that not more than 3 of the X residues are isoleucine.

3. The antimicrobial peptide of claim 2, wherein only one of X$_1$, X$_2$, X$_3$ and X$_4$ is selected from the group consisting of glycine, serine and threonine.

4. The antimicrobial peptide of claim 3, wherein said peptide comprises the amino acid sequence set forth in SEQ ID NO:17.

5. The antimicrobial peptide of claim 4, wherein said peptide consists essentially of the amino acid sequence set forth in SEQ ID NO:17.

6. The antimicrobial peptide of claim 1, wherein the carboxy terminus of said peptide is amidated.

7. An antimicrobial formulation, comprising:
   an antimicrobial polypeptide comprising the sequence, as set forth in SEQ ID NO:1, KNLRRX$_1$X$_2$RKX$_3$X$_4$HIIKKYG;
   wherein X$_1$, X$_2$, X$_3$ and X$_4$ are independently selected from the group consisting of glycine, threonine, serine, glutamic acid, aspartic acid, isoleucine, D-alanine and D-isoleucine, with the proviso that not more than 3 of the X residues are isoleucine; and
   a pharmaceutically acceptable carrier.

8. The antimicrobial formulation of claim 7, wherein X$_1$, X$_2$, X$_3$ and X$_4$ are independently selected from the group consisting of glycine, threonine, serine and, isoleucine, with the proviso that not more than 3 of the X residues are isoleucine.

9. The antimicrobial formulation of claim 8, wherein only one of X$_1$, X$_2$, X$_3$ and X$_4$ is selected from the group consisting of glycine, serine and threonine.

10. The antimicrobial formulation of claim 9, wherein said peptide comprises the amino acid sequence set forth in SEQ ID NO:17.

11. The antimicrobial formulation of claim 10, wherein said peptide consists essentially or the amino acid sequence set forth in SEQ ID NO:17.

12. The antimicrobial formulation of claim 7, wherein the carboxy terminus of the peptide is amidated.

13. The antimicrobial formulation of claim 7, wherein said pharmaceutically acceptable carrier comprises a chelating agent.

14. The antimicrobial formulation of claim 13, wherein said chelating agent is citrate.

15. The antimicrobial formulation of claim 7, further comprising a second antimicrobial agent.

16. The antimicrobial formulation of claim 15, wherein said second antimicrobial agent is an antibiotic.

17. The antimicrobial formulation of claim 7, wherein said formulation is suitable for aerosol delivery of said antimicrobial peptide.

18. A method for treating a microbial infection, the method comprising:

contacting a microbial population with an antimicrobial polypeptide comprising the sequence, as set forth in SEQ ID NO:1, KNLRRX$_1$X$_2$RKX$_3$X$_4$HIIKKYG;

wherein X$_1$, X$_2$, X$_3$ and X$_4$ are independently selected from the group consisting of glycine, threonine, serine, glutamic acid, aspartic acid, isoleucine, D-alanine and D-isoleucine, with the proviso that not more than 3 of the X residues are isoleucine.

19. The method of claim 18, wherein X$_1$, X$_2$, X$_3$ and X$_4$ are independently selected from the group consisting of glycine, threonine, serine and, isoleucine, with the proviso that not more than 3 of the X residues are isoleucine.

20. The method of claim 19, wherein only one of X$_1$, X$_2$, X$_3$ and X$_4$ is selected from the group consisting of glycine, serine and threonine.

21. The method of claim 20, wherein said peptide comprises the amino acid sequence set forth in SEQ ID NO:17.

22. The method of claim 21, wherein said peptide consists essentially of the amino acid sequence set forth in SEQ ID NO:17.

23. The method of claim 18, wherein said microbial population comprises gram negative bacteria.

24. The method of claim 23, wherein said gram negative bacteria are one or more of *Pseudomonas aeruginosa, Chlamydia trachomatis, Escherichia coli* and *Stenotrophomonas maltophilia.*

25. The method of claim 18, wherein the carboxy terminus of the peptide is amidated.

26. The method of claim 18, wherein said peptide is formulated in a pharmaceutically acceptable carrier comprising a chelating agent.

27. The method of claim 26, wherein said chelating agent is citrate.

* * * * *

```
                            SEQUENCE LISTING

<160> NUMBER OF SEQ ID NOS: 37

<210> SEQ ID NO 1
<211> LENGTH: 18
<212> TYPE: PRT
<213> ORGANISM: Artificial Sequence
<220> FEATURE:
<223> OTHER INFORMATION: Synthetic antimicrobial peptide
<221> NAME/KEY: VARIANT
<222> LOCATION: (1)...(18)
<223> OTHER INFORMATION: Xaa = glycine, threonine, serine, glutamic
      acid, aspartic acid, D-alanine, D-isoleucine

<400> SEQUENCE: 1

Lys Asn Leu Arg Arg Xaa Xaa Arg Lys Xaa Xaa His Ile Ile Lys Lys
 1               5                  10                  15

Tyr Gly

<210> SEQ ID NO 2
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 2

Lys Asn Leu Arg Arg Ile Ile Arg Lys Ile Ile His Ile Ile Lys Lys
 1               5                  10                  15

Tyr Gly

<210> SEQ ID NO 3
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 3

Lys Asn Leu Arg Arg Gly Ile Arg Lys Ile Ile His Ile Ile Lys Lys
 1               5                  10                  15

Tyr Gly

<210> SEQ ID NO 4
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 4

Lys Asn Leu Arg Arg Thr Ile Arg Lys Ile Ile His Ile Ile Lys Lys
 1               5                  10                  15

Tyr Gly
```

```
<210> SEQ ID NO 5
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 5

Lys Asn Leu Arg Arg Ser Ile Arg Lys Ile Ile His Ile Ile Lys Lys
 1               5                  10                  15

Tyr Gly

<210> SEQ ID NO 6
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 6

Lys Asn Leu Arg Arg Glu Ile Arg Lys Ile Ile His Ile Ile Lys Lys
 1               5                  10                  15

Tyr Gly

<210> SEQ ID NO 7
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 7

Lys Asn Leu Arg Arg Asp Ile Arg Lys Ile Ile His Ile Ile Lys Lys
 1               5                  10                  15

Tyr Gly

<210> SEQ ID NO 8
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-alanine

<400> SEQUENCE: 8

Lys Asn Leu Arg Arg Ala Ile Arg Lys Ile Ile His Ile Ile Lys Lys
 1               5                  10                  15

Tyr Gly

<210> SEQ ID NO 9
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-isoleucine

<400> SEQUENCE: 9

Lys Asn Leu Arg Arg Ile Ile Arg Lys Ile Ile His Ile Ile Lys Lys
 1               5                  10                  15

Tyr Gly

<210> SEQ ID NO 10
```

```
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 10

Lys Asn Leu Arg Arg Ile Gly Arg Lys Ile Ile His Ile Ile Lys Lys
 1               5                  10                  15

Tyr Gly

<210> SEQ ID NO 11
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 11

Lys Asn Leu Arg Arg Ile Thr Arg Lys Ile Ile His Ile Ile Lys Lys
 1               5                  10                  15

Tyr Gly

<210> SEQ ID NO 12
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 12

Lys Asn Leu Arg Arg Ile Ser Arg Lys Ile Ile His Ile Ile Lys Lys
 1               5                  10                  15

Tyr Gly

<210> SEQ ID NO 13
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 13

Lys Asn Leu Arg Arg Ile Glu Arg Lys Ile Ile His Ile Ile Lys Lys
 1               5                  10                  15

Tyr Gly

<210> SEQ ID NO 14
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 14

Lys Asn Leu Arg Arg Ile Asp Arg Lys Ile Ile His Ile Ile Lys Lys
 1               5                  10                  15

Tyr Gly

<210> SEQ ID NO 15
<211> LENGTH: 18
<212> TYPE: PRT
<213> ORGANISM: Artificial Sequence
<220> FEATURE:
```

<223> OTHER INFORMATION: Synthetic antimicrobial peptide
<223> OTHER INFORMATION: D-alanine

<400> SEQUENCE: 15

Lys Asn Leu Arg Arg Ile Ala Arg Lys Ile Ile His Ile Ile Lys Lys
 1               5                   10                  15

Tyr Gly

<210> SEQ ID NO 16
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-isoleucine

<400> SEQUENCE: 16

Lys Asn Leu Arg Arg Ile Ile Arg Lys Ile Ile His Ile Ile Lys Lys
 1               5                   10                  15

Tyr Gly

<210> SEQ ID NO 17
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 17

Lys Asn Leu Arg Arg Ile Ile Arg Lys Gly Ile His Ile Ile Lys Lys
 1               5                   10                  15

Tyr Gly

<210> SEQ ID NO 18
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 18

Lys Asn Leu Arg Arg Ile Ile Arg Lys Thr Ile His Ile Ile Lys Lys
 1               5                   10                  15

Tyr Gly

<210> SEQ ID NO 19
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 19

Lys Asn Leu Arg Arg Ile Ile Arg Lys Ser Ile His Ile Ile Lys Lys
 1               5                   10                  15

Tyr Gly

<210> SEQ ID NO 20
<211> LENGTH: 18
<212> TYPE: PRT
<213> ORGANISM: Artificial Sequence
<220> FEATURE:
<223> OTHER INFORMATION: Synthetic antimicrobial peptide

```
<400> SEQUENCE: 20

Lys Asn Leu Arg Arg Ile Ile Arg Lys Glu Ile His Ile Ile Lys Lys
 1               5                  10                  15

Tyr Gly

<210> SEQ ID NO 21
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 21

Lys Asn Leu Arg Arg Ile Ile Arg Lys Asp Ile His Ile Ile Lys Lys
 1               5                  10                  15

Tyr Gly

<210> SEQ ID NO 22
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-alanine

<400> SEQUENCE: 22

Lys Asn Leu Arg Arg Ile Ile Arg Lys Ala Ile His Ile Ile Lys Lys
 1               5                  10                  15

Tyr Gly

<210> SEQ ID NO 23
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-isoleucine

<400> SEQUENCE: 23

Lys Asn Leu Arg Arg Ile Ile Arg Lys Ile Ile His Ile Ile Lys Lys
 1               5                  10                  15

Tyr Gly

<210> SEQ ID NO 24
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 24

Lys Asn Leu Arg Arg Ile Ile Arg Lys Ile Gly His Ile Ile Lys Lys
 1               5                  10                  15

Tyr Gly

<210> SEQ ID NO 25
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 25
```

```
Lys Asn Leu Arg Arg Ile Ile Arg Lys Ile Thr His Ile Ile Lys Lys
1               5                   10                  15

Tyr Gly

<210> SEQ ID NO 26
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 26

Lys Asn Leu Arg Arg Ile Ile Arg Lys Ile Ser His Ile Ile Lys Lys
1               5                   10                  15

Tyr Gly

<210> SEQ ID NO 27
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 27

Lys Asn Leu Arg Arg Ile Ile Arg Lys Ile Glu His Ile Ile Lys Lys
1               5                   10                  15

Tyr Gly

<210> SEQ ID NO 28
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 28

Lys Asn Leu Arg Arg Ile Ile Arg Lys Ile Asp His Ile Ile Lys Lys
1               5                   10                  15

Tyr Gly

<210> SEQ ID NO 29
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-alanine

<400> SEQUENCE: 29

Lys Asn Leu Arg Arg Ile Ile Arg Lys Ile Ala His Ile Ile Lys Lys
1               5                   10                  15

Tyr Gly

<210> SEQ ID NO 30
<211> LENGTH: 18
<212> TYPE: PRT
<213> ORGANISM: Artificial Sequence
<220> FEATURE:
<223> OTHER INFORMATION: Synthetic antimicrobial peptide
<223> OTHER INFORMATION: D-isoleucine

<400> SEQUENCE: 30

Lys Asn Leu Arg Arg Ile Ile Arg Lys Ile Ile His Ile Ile Lys Lys
1               5                   10                  15
```

Tyr Gly

<210> SEQ ID NO 31
<211> LENGTH: 18
<212> TYPE: PRT
<213> ORGANISM: Artificial Sequence
<220> FEATURE:
<223> OTHER INFORMATION: Synthetic antimicrobial peptide
<221> NAME/KEY: AMIDATION
<222> LOCATION: (18)...(18)
<223> OTHER INFORMATION: G-CONH2

<400> SEQUENCE: 31

Lys Asn Leu Arg Arg Ile Ile Arg Lys Gly Ile His Ile Ile Lys Lys
 1               5                  10                  15

Tyr Gly

<210> SEQ ID NO 32
<211> LENGTH: 18
<212> TYPE: PRT
<213> ORGANISM: Artificial Sequence
<220> FEATURE:
<223> OTHER INFORMATION: Synthetic antimicrobial peptide

<400> SEQUENCE: 32

Lys Asn Leu Arg Arg Ile Ile Arg Lys Gly Ile Arg Ile Ile Lys Lys
 1               5                  10                  15

Tyr Gly

<210> SEQ ID NO 33
<211> LENGTH: 18
<212> TYPE: PRT
<213> ORGANISM: Artificial Sequence
<220> FEATURE:
<223> OTHER INFORMATION: Synthetic antimicrobial peptide
<221> NAME/KEY: AMIDATION
<222> LOCATION: (18)...(18)
<223> OTHER INFORMATION: G-CONH2

<400> SEQUENCE: 33

Lys Asn Leu Arg Arg Ile Ile Arg Lys Gly Ile Arg Ile Ile Lys Lys
 1               5                  10                  15

Tyr Gly

<210> SEQ ID NO 34
<211> LENGTH: 18
<212> TYPE: PRT
<213> ORGANISM: Artificial Sequence
<220> FEATURE:
<223> OTHER INFORMATION: Synthetic variant of G10 novispirin peptide

<400> SEQUENCE: 34

Lys Arg Leu Arg Arg Ile Ile Arg Lys Gly Ile His Ile Ile Lys Lys
 1               5                  10                  15

Tyr Gly

<210> SEQ ID NO 35
<211> LENGTH: 18
<212> TYPE: PRT
<213> ORGANISM: Artificial Sequence
<220> FEATURE:
<223> OTHER INFORMATION: Synthetic variant of G10 novispirin
<221> NAME/KEY: AMIDATION
<222> LOCATION: (18)...(18)
<223> OTHER INFORMATION: G-CONH2

```
<400> SEQUENCE: 35

Lys Arg Leu Arg Arg Ile Ile Arg Lys Gly Ile His Ile Ile Lys Lys
1               5                   10                  15

Tyr Gly

<210> SEQ ID NO 36
<211> LENGTH: 18
<212> TYPE: PRT
<213> ORGANISM: Artificial Sequence
<220> FEATURE:
<223> OTHER INFORMATION: Synthetic variant of G10 novispirin

<400> SEQUENCE: 36

Arg Arg Leu Arg Arg Ile Ile Arg Lys Gly Ile Arg Ile Ile Lys Lys
1               5                   10                  15

Tyr Gly

<210> SEQ ID NO 37
<211> LENGTH: 18
<212> TYPE: PRT
<213> ORGANISM: Artificial Sequence
<220> FEATURE:
<223> OTHER INFORMATION: Synthetic variant of G10 novispirin
<221> NAME/KEY: AMIDATION
<222> LOCATION: (18)...(18)
<223> OTHER INFORMATION: G-CONH2

<400> SEQUENCE: 37

Arg Arg Leu Arg Arg Ile Ile Arg Lys Gly Ile Arg Ile Ile Lys Lys
1               5                   10                  15

Tyr Gly
```